(12) United States Patent
Zebala et al.

(10) Patent No.: US 8,349,837 B2
(45) Date of Patent: Jan. 8, 2013

(54) PHARMACEUTICAL COMPOSITION COMPRISING RACEMIC AMINOPTERIN

(75) Inventors: John A. Zebala, Sammamish, WA (US); Dean Y. Maeda, Seattle, WA (US); Joel R. Morgan, Kent, WA (US); Stuart J. Kahn, Seattle, WA (US)

(73) Assignee: Aminopterin, LLC, Auburn, WA (US)

( * ) Notice: Subject to any disclaimer, the term of this patent is extended or adjusted under 35 U.S.C. 154(b) by 162 days.

(21) Appl. No.: 12/692,593

(22) Filed: Jan. 23, 2010

(65) Prior Publication Data

US 2010/0190798 A1 Jul. 29, 2010

Related U.S. Application Data

(60) Provisional application No. 61/147,093, filed on Jan. 24, 2009.

(51) Int. Cl.
*A61K 31/495* (2006.01)
*A01N 43/58* (2006.01)
*A01N 43/60* (2006.01)
*C07D 475/00* (2006.01)

(52) U.S. Cl. ...................................... 514/249; 544/260
(58) Field of Classification Search .................. 514/249; 544/260

See application file for complete search history.

(56) References Cited

U.S. PATENT DOCUMENTS

| | | | | |
|---|---|---|---|---|
| 4,746,659 | A | * | 5/1988 | DeGraw et al. ............... 514/249 |
| 6,720,304 | B1 | * | 4/2004 | Sinn et al. ..................... 514/15.2 |
| 7,312,217 | B2 | | 12/2007 | Zebala |
| 2006/0234909 | A1 | | 10/2006 | Newman et al. |

OTHER PUBLICATIONS

WebMD, Rheumatoid Arthritis [Downloaded Oct. 25, 2011] [Retrieved from internet <URL: http://www.webmd.com/rheumatoid-arthritis/tc/rheumatoid-arthritis-medications?page=2 >], 0 pages.*
Merck Index, Aminopterin (Knovel 2006 and 2012) [Downloaded Feb. 27, 2012] (internet URL cited in action), 2 pages.*
Seeger et al. (J. Am. Chem. Soc., Analogs of Pteroylglutamic Acid III. 4-Amino Derivatives, 71 (1949) 1753-1758 [Downloaded Feb. 27, 2012] [Retrieved from internet <URL: http://pubs.acs.org/doi/pdf/10.1021/ja01173a061 >]), 6 pages.*
PubChem (methotrexate polyglutamate—compound summary [Downloaded Feb. 27, 2012] [Retrieved from internet <URL: http://pubchem.ncbi.nlm.nih.gov/summary/summary.cgi?cid=4112& loc=ec_rcs >]), 4 pages.*
Innes et al. (The Hematologic Changes Induced in Guinea Pigs by the Prolonged Administration of Pteroyl Glutamic Acid Antagonists, The Journal of Laboratory and Clinical Medicine (Jul. 1949) 34(7): 883-901), 19 pages.*
Knovel, Merck Index, Folic Acid (Merck Sharp & Dohme Corp., 2006, 2012), 3 pages.*

(Continued)

*Primary Examiner* — Jason M Sims
*Assistant Examiner* — Miriam A Levin
(74) *Attorney, Agent, or Firm* — Jeffrey B. Oster

(57) ABSTRACT

There is disclosed a pharmaceutical composition comprising racemic aminopterin or pharmaceutically acceptable salts thereof. There is further disclosed a method to treat a disorder in a patient comprising administering a therapeutically effective amount of racemic aminopterin or pharmaceutically acceptable salts of racemic aminopterin. More particularly, there is disclosed a method for treating disorders modulated by at least dihydrofolate reductase activity, such as cancers and inflammatory disorders, wherein the method comprises administering to a patient in need thereof a therapeutically effective amount of racemic aminopterin or a pharmaceutically acceptable salt thereof.

18 Claims, 5 Drawing Sheets

OTHER PUBLICATIONS

Miles J. Sweet, The Patentability of Chiral Drugs Post-KSR: The More Things Change, the More They Stay the Same, Berkeley Technology Law Journal 24:1 (2009), 19 pages.* duVigneaud and Meyer, "The Racemization of Amino Acids in Aqueous Solution by Acetic Anhydride" pp. 295-308, 1932 or 1933.

Dakin and West, "A General Reaction of Amino Acids II" pp. 745-756, 1928 or 1929.

Lepschy et al. Liebigs Ann. Chem. 1974, 1753-1762.

Luo et al. J. Am. Chem. Soc. 119:10004-10013, 1997.

Temple et al. J. Org. Chem., 46:3666-3667, 1981.

Yamada et al. J. Org. Chem., 48:843-846, 1983.

Arnow and Opsahl, "Racemazaion of Glutamic Acid with Alkalies" Science, 93:2409-2410, 1941.

McGuire et al. J. Biol. Chem. 255:5776-5788, 1980.

Cramer et al. "Occurrence and Significance of D-Methotrexate as a Contaminant of Commercial Methotrexate" Cancer Res. 44:1843-1846, 1984.

Hendel and brodthagen "Entero-hepatic Cycling of Methotrexate Estimated by Use of the D-Isomer as a Reference Market" Eur. J. Clin. Pharmacol. 26:103-107, 1984.

Itoh et al. "Stereoselectivity of the Folate Transporter in Rabbit Small Intestine: Studies with Amethoterin Enantiomers" Chirality 13:164-169, 2001.

Lee et al. "Folic Acid Antagonists. Methotrexate Analogs Containing Spurious Amino Acids. Dichlorohomofolic Acid" J. Med. Chem. 17:326-330, 1974.

Menter et al. "Intestinal Transport of Aminopterin Enantiomers in Dogs and Humans with Psoriasis is Stereoselective: Evidence for a Mechanism Involving the Proton-Coupled Folate Transporter" J. Pham. Exp. Therapeutics 342:696-708, 2012.

Narawa-1 et al. "Stereoselectivity of the Reduced Folate Carrier in Caco-2 Cells" Chirality 16:444-449, 2005.

Narawa-2 et al. "Chiral Recognition of Amethopterin Enantiomers by the Reduced Folate Carrier in Caco-2 Cells" Drug Metab. Pharmacokinet. 22:33-40, 2007.

Narawa and Itoh "Stereoselective Transport of Amethopterin Enantiomers by the Proton-coupled Folate Transporter" Drug Metab. Pharmacokinet. 25:283-289, 2010.

* cited by examiner

US 8,349,837 B2

PHARMACEUTICAL COMPOSITION COMPRISING RACEMIC AMINOPTERIN

CROSS REFERENCE TO RELATED APPLICATION

The present patent application claims priority to U.S. Provisional Patent Application 61/147,093 filed on 24 Jan. 2009.

This invention was made with government support under grants 1R43AI068282, 3R43AI068282-01S1, 3R43AI068282-S2, 5R43AR056547 awarded by the National Institutes of Health. The government has certain rights to this invention.

TECHNICAL FIELD

The present disclosure provides pharmaceutical compositions containing racemic aminopterin or pharmaceutically acceptable salts of racemic aminopterin. The present disclosure further provides a method to treat a disorder in a patient comprising administering a therapeutically effective amount of racemic aminopterin or pharmaceutically acceptable salts of racemic aminopterin. More particularly, the present disclosure provides a method for treating disorders modulated by at least dihydrofolate reductase activity, such as cancers and inflammatory disorders, wherein the method comprises administering to a patient in need thereof a therapeutically effective amount of racemic aminopterin or a pharmaceutically acceptable salt thereof.

BACKGROUND

An enantiomer is one of two stereoisomers that are not superimposable mirror images of each other, much as one's left and right hands are mirror images but are not superimposable. Enantiomers have essentially identical physical (except for their ability to rotate plane-polarized light by equal amounts but in opposite directions) and chemical (except in a chiral environment) properties. A mixture of equal parts of an optically active isomer and its enantiomer is a racemate, and has a net rotation of plane-polarized light of zero.

Many drug molecules are chiral, and synthetic chemical reactions involved in their production often produce racemates. However, since many biomolecules are chiral, there may be a marked difference in the effects of the two enantiomers in a racemate on living beings, including human beings. Differences in biologic effects, if any, between enantiomers in a racemate or between separate enantiomers and their racemate combination, is extremely difficult to predict a priori, and may include no differences, different pharmacokinetics, and quantitatively or qualitatively different pharmacologic or toxicologic effects.

For example, cases in which both enantiomers in a racemate had similar biologic activity include: both enantiomers of dobutamine which are positive inotropes; both ibuprofen enantiomers which are anti-inflammatory agents; both enantiomers of warfarin and phenprocoumon which are anticoagulants; and the enantiomers of bupivicaine which both produce local anesthesia.

Alternatively, cases in which one enantiomer in a racemate had biologic activity and the other had no activity include: the enantiomers of the quinolones (e.g., l-propranolol is a β-blocker and d-propranolol is not) and the β-lactam antibiotics.

In still other examples, cases in which each enantiomer in a racemate had completely different activities include racemic sotalol, where d-sotalol is a type 3 antiarrhythmic agent and l-sotalol is a β-blocker. In these cases, there are even instances in which toxicity has been linked to the enantiomer not responsible for the desirable activity of the racemate. For example, granulocytopenia is related to the d-isomer of levodopa; vomiting is caused by the d-isomer of levamisole; and myasthenia gravis symptoms were no longer observed when the d-isomer was removed from racemic carnitine.

Due to the potential for the enantiomers in a racemate to have different pharmacological effects on living beings, it is generally desirable to develop a drug manufacturing process that produces substantially only a single enantiomer. A disadvantage of this approach is the higher cost associated with a process that produces substantially a single enantiomer as compared to a process that produces the racemate.

Whereas choosing to develop a drug as a racemate may reduce the post-approval manufacturing costs relative to producing one of its enantiomers in substantially pure form, this is countered in the pre-approval phase by the higher costs associated with the increased regulatory burden of developing the racemate. The increased regulatory burden of the racemate arises from additional testing and development requirements in manufacturing control, pharmacologic and toxicologic assessment, characterization of metabolism and distribution, and clinical evaluation.

"Aminopterin [54-62-6]N-[4-[[(2,4-Diamino-6-pterdinyl)methyl]amino]benzoyl]-L-glutamic acid" (page 83, The Merck Index, 13$^{th}$ Edition, Merck & Co., Inc., Whitehouse Station, N.J. 2001) is described and used in the art as the L enantiomer. According to *The Merck Index*, aminopterin is prepared "from 2,4,5,6-tetraminopyrimidine sulfate, 2,3-dibromopropionaldehyde and p-aminobenzoylglutamic acid: Seeger et al., *J. Am. Chem. Soc.* 69, 2567 (1947); from 6-(bromomethyl)-2,4-diaminopteridine HBr: Piper, Montgomery, *J. Heterocycl. Chem.* 11, 279 (1974)." Therefore, the use of the term "aminopterin" in the art refers to the L enantiomer.

It would therefore be a significant advantage if a drug could be developed as its racemate, while obviating many of the additional testing and development costs relative to developing it as a single enantiomer. It would be a further advantage if the racemate (i.e., the combination of the enantiomers) had additional favorable biologic properties compared to the enantiomer responsible for the majority of the desired biologic effects. Aminopterin, or N-4-[[2,4-diamino-6-pteridinyl)-methyl]amino]benzoy-1]-L-glutamic acid, is a potent antifolate useful for treating a variety of human and animal diseases. It is optically active, having a single chiral center.

SUMMARY

The present disclosure provides a pharmaceutical composition comprising racemic aminopterin or a pharmaceutically acceptable salt of racemic aminopterin. Preferably, racemic aminopterin or pharmaceutically acceptable salt of racemic aminopterin comprises D-aminopterin and L-aminopterin, wherein there is 15% to 85% D-aminopterin present in the racemic aminopterin. More preferably, there is 25% to 75% D-aminopterin present in the racemic aminopterin or pharmaceutically acceptable salt of racemic aminopterin. More preferably still, there is 35% to 65% D-aminopterin present in the racemic aminopterin. Most preferably, there is 45% to 55% D-aminopterin present in the racemic aminopterin or pharmaceutically acceptable salt of racemic aminopterin. Preferably, the pharmaceutical composition is adapted for oral administration. More preferably, the pharmaceutical composition is a tablet or capsule dosage form and further comprising pharmaceutical excipients. Preferably, the racemic aminopterin pharmaceutically acceptable salt is a disodium salt. Preferably, the racemic aminopterin in the pharmaceutical composition is present in an amount from 0.01 mg to 4 mg. Preferably, the pharmaceutical composition further comprises L-aminopterin.

The present disclosure further provides a method for treating disorders modulated by at least dihydrofolate reductase activity, said method comprises administering to a patient in need thereof a therapeutically effective amount of racemic aminopterin or a pharmaceutically acceptable salt thereof. The racemic aminopterin is preferably administered orally.

Preferably, the disorders modulated by at least dihydrofolate reductase activity are selected from the group consisting of cancers and inflammatory disorders. More preferably, the cancers are selected from the group consisting of leukemia, lymphoma, breast cancer, squamous cell tumors of the head and neck, choriocarcinoma, and endometrial cancer. More preferably, the inflammatory disorders are selected from the group consisting of asthma, multiple sclerosis, rheumatoid arthritis, juvenile rheumatoid arthritis, restenosis, psoriasis, psoriatic arthritis, arthritis, atopic dermatitis, chronic obstructive pulmonary disease, inflammatory bowel disease, pulmonary fibrosis, polycystic kidney disease, bronchopulmonary dysplasia, pneumoconiosis, systemic lupus erythematosus, polymyositis, graft-versus-host disease, transplant rejection, bovine acute pneumonic pasteurellosis and canine atopic dermatitis.

Preferably, racemic aminopterin or pharmaceutically acceptable salt of racemic aminopterin comprises D-aminopterin and L-aminopterin, wherein there is 15% to 85% D-aminopterin present in the racemic aminopterin. More preferably, there is 25% to 75% D-aminopterin present in the racemic aminopterin or pharmaceutically acceptable salt of racemic aminopterin. More preferably still, there is 35% to 65% D-aminopterin present in the racemic aminopterin. Most preferably, there is 45% to 55% D-aminopterin present in the racemic aminopterin or pharmaceutically acceptable salt of racemic aminopterin.

The disclosed pharmaceutical compositions of racemic aminopterin provide commercial and biologic advantages, including (i) lower production costs compared to enantiopure drugs; (ii) reduced regulatory burden compared to other racemic drugs; and (iii) enhanced systemic exposure of the active L isomer compared to pharmaceutical compositions of only the L isomer.

DETAILED DESCRIPTION

Figure 1:
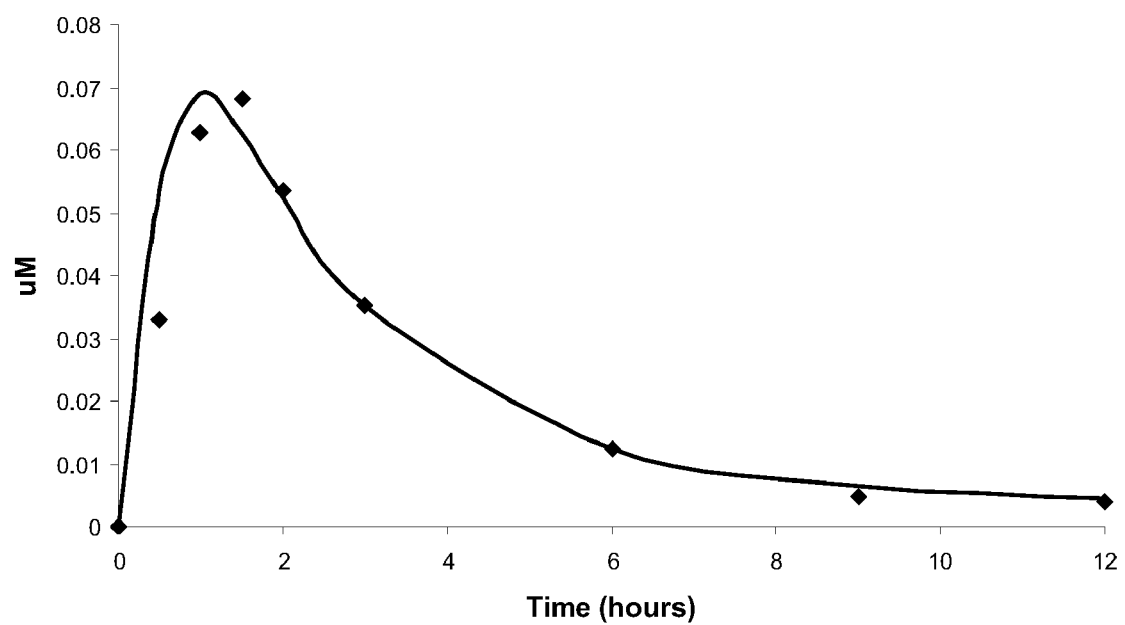
FIG. 1 is a graphical depiction of mean plasma levels of the L-isomer following oral administration of L-aminopterin to 10 Beagle dogs described in Example 4.

The present disclosure provides pharmaceutical compositions comprising racemic aminopterin and pharmaceutically acceptable salts thereof. It has been unexpectedly discovered that absorption of orally administered racemic aminopterin is selective for the L-isomer, with substantially no detectable D-isomer in the circulation. The newly discovered selectivity for the L-isomer obviates many of the additional testing, development costs and regulatory burden of the racemate because the D-isomer need not be considered in pharmacologic and toxicologic assessments, characterizations of metabolism and distribution, and clinical evaluations. This represents a significant commercial advantage. It has been further unexpectedly discovered that the systemic exposure of the L-isomer from orally administered racemic aminopterin is enhanced relative to the oral administration of the pure L-isomer.

As used herein, 'L-aminopterin' or the 'L-isomer' means the free acid form of N-4-[[2,4-diamino-6-pteridinyl)-methyl]amino]benzoy-1]-L-glutamic acid. The L-isomer causes a positive rotation in plane-polarized light; $[\alpha]_D^{25}=+18°±2°$ (c=0.1 in water for the disodium salt). As used herein, 'D-aminopterin' or the 'D-isomer' means the free acid form of N-4-[[2,4-diamino-6-pteridinyl)-methyl]amino]benzoy-1]-D-glutamic acid. The D-isomer causes a negative rotation in plane-polarized light; $[\alpha]_D^{25}=-18°±2°$ (c=0.1 in water for the disodium salt). As used herein, 'racemic aminopterin', 'aminopterin racemate', 'rac-aminopterin' or 'L/D-aminopterin' means a substantially equal mixture of L-aminopterin and D-aminopterin. Racemic aminopterin does not cause a detectable rotation in plane-polarized light. Racemic aminopterin may form a salt with various inorganic and organic acids and bases, which salts may be prepared by conventional methods. The disodium salt is preferred.

Rac-aminopterin inhibits enzymes involved in purine and pyrimidine metabolism, including dihydrofolate reductase, which leads indirectly to the extracellular release of adenosine. Adenosine is a powerful anti-inflammatory autocoid that regulates innate immunity (reviewed by Hasko and Cronstein, (2004) "Adenosine: an endogenous regulator of innate immunity" *Trends Immunol.*, 25/1:33-39) and that decreases the activation of antigen-stimulated cells, decreases the expression of adhesion molecules, and possibly induces T cell apoptosis (Cronstein et al., *Proc. Natl. Acad. Sci. USA* (1991), 88: 2441; Cronstein et al., *J. Clin. Invest.* (1993), 92/6:2675; Genesteir et al., *J. Clin. Invest.* (1998), 102:322-328; Morabito et al., *J. Clin. Invest.* (1998), 101:295-300; Paillot et al., *Transplant Proc.* (1998), 30/5:2348-50; and Johnston et al., *Clin. Immunol.* (2005), 114/2:154-63).

The pivotal role of adenosine in human inflammatory disorders, such as rheumatoid arthritis and psoriasis, is now appreciated. Adenosine can be measured directly in the synovial fluid collected from patients with rheumatoid arthritis (Ottonello et al., *Rheumatology* (2002), 41:1249-1260).

As used herein, the term "disorders treated by modulating dihydrofolate reductase activity" refers to a disorder, disease or condition where modulating dihydrofolate reductase activity is an effective means of alleviating the disorder or one or more of the biological manifestations of the disease or disorder; or interferes with one or more points in the biological cascade leading to the disorder or responsible for the underlying disorder; or alleviates one or more symptoms of the disorder. Thus, the disorders subject to modulating dihydrofolate reductase activity include those for which:

(a) the lack of dihydrofolate reductase activity is a cause of the disorder or one or more of the biological manifestations, whether the activity was altered genetically, by infection, by irritation, by internal stimulus or by some other cause;

(b) the disease or disorder or the observable manifestation or manifestations of the disease or disorder are alleviated by decreasing dihydrofolate reductase activity. The presence of dihydrofolate reductase activity need not be causally related to the disease or disorder or the observable manifestations thereof; or (c) dihydrofolate reductase activity interferes with part of the biochemical or cellular cascade that results in or relates to the disease or disorder. In this respect, the dihydrofolate reductase activity alters the cascade, and thus controls the disease, condition or disorder.

Disorders treated by modulating dihydrofolate reductase activity with rac-aminopterin include cancers: for example, leukemia, lymphoma, breast cancer, squamous cell tumors of the head and neck, choriocarcinoma, endometrial cancer; and inflammatory disorders: for example, asthma, multiple sclerosis, rheumatoid arthritis, juvenile rheumatoid arthritis, restenosis, psoriasis, psoriatic arthritis, arthritis, atopic dermatitis, chronic obstructive pulmonary disease, inflammatory bowel disease, pulmonary fibrosis, polycystic kidney disease, bronchopulmonary dysplasia, pneumoconiosis, systemic lupus erythematosus, polymyositis, graft-versus-host disease, transplant rejection, bovine acute pneumonic pasteurellosis and canine atopic dermatitis.

In a preferred embodiment, the present disclosure provides a method for treating disorders modulated by at least dihydrofolate reductase activity, said method comprising administering to a patient in need thereof a therapeutically effective amount of racemic aminopterin, or a pharmaceutically acceptable salt thereof. Dihydrofolate reductase is said to be inhibited in a patient if the percent inhibition comprises the range of 5% to 100%.

The term "patient" is an animal or a human. The term "therapeutically effective amount" means the dosage (dose or amount, and frequency) of rac-aminopterin which, directly or indirectly, kills inflammatory cells, arrests the accumulation of inflammatory cells, or reduces the accumulation of inflammatory cells in a human or other mammal afflicted with an inflammatory inflammatory disorder, such as, for example, arthritis of undefined etiology, rheumatoid arthritis, juvenile rheumatoid arthritis, atopic dermatitis, bronchopulmonary dysplasia, inflammatory bowel disease, psoriatic arthritis and psoriasis, or a animal with, for example, canine atopic dermatitis or bovine acute pneumonic pasteurellosis. The term "therapeutically effective amount" shall also mean the dosage of rac-aminopterin which, directly or indirectly, reduces or increases the activity of molecules secreted by inflammatory and/or non-inflammatory cells participating in an inflammatory disorder in a human or mammal, such that the amount of antifolate arrests, reduces, or eliminates altogether a degree of pathologic inflammation associated with the inflammatory disorder. Typically, a therapeutically effective amount will also eliminate, reduce, or prevent the progression of, one or more disease manifestations. A skilled clinician will recognize that in many cases rac-aminopterin may not provide a cure, but may only provide partial benefit. Furthermore, the skilled clinician will recognize that because individual patients and disease states may vary, some patients may receive little, or no benefit at all. A dosage of rac-aminopterin that "kills", "arrests", "reduces" or "eliminates" as described above, in a least some patients, is considered therapeutically effective. The dose magnitude of a therapeutically effective amount of rac-aminopterin in the acute or chronic management of an inflammatory disorder will vary with the severity of the inflammatory disorder to be treated and the route of administration.

The dosage and dose rate of rac-aminopterin will depend on a variety of factors, such as the weight and calculated surface area of the patient, the specific pharmaceutical composition used, the object of the treatment, i.e., therapy or prophylaxis, the nature of the disease to be treated, the judgment of the treating physician, and the response of the individual patient. With leucovorin rescue, large doses of rac-aminopterin are possible.

In general, a therapeutically effective amount of rac-aminopterin, without leucovorin rescue, will be a dose of rac-aminopterin from 0.001-0.5, 0.001-0.27 mg/kg, 0.005-0.06 mg/kg, and most preferably 0.010-0.06 mg/kg for inflammatory indications, and 0.13-0.27 mg/kg for oncology indications, given as a single or divided dose.

Patients may be upward titrated from below to within these dose ranges to a satisfactory control of disease manifestations. Once improvement in the patient's condition has occurred, a maintenance dosage of a composition of this disclosure is administered, if necessary. Subsequently, the dose rate may be reduced by reducing the dose or frequency of administration, or a combination of both, as a function of the symptoms, to a level at which the improved condition is retained. When the symptoms have been alleviated to the desired level, the physician may elect to cease treatment. Patients may, however, require intermittent treatment upon any recurrence of disease symptoms, or prophylactically scheduled treatments as required. The therapeutically effective amount of rac-aminopterin may optionally be administered prior to, contemporaneous with, or after at least one therapeutically effective dose of leucovorin or folic acid.

The present disclosure further provides a method for treating an inflammatory disorder in a patient with uninterrupted cycles of rac-aminopterin doses, wherein the doses comprise a therapeutically effective amount of rac-aminopterin. Uninterrupted means that rac-aminopterin doses are repetitively administered to a patient for at least 4 cycles, 12 cycles, 24 cycles, and most preferably greater than 52 cycles, wherein the periodicity of the cycles is constant, and wherein the greatest duration between the last dose of one cycle and the first dose of the next cycle does not exceed 21 days, 14 days, and most preferably 7 days. Within this definition, "periodicity of the cycles is constant" means that the duration between corresponding doses in consecutive cycles is constant to within a 12 hour range. For example, if the periodicity is denoted to be 7 days (i.e., 168 hours), then the phrase "periodicity of the cycles is constant" will be construed to mean that the duration between corresponding doses in consecutive cycles may range from 162 to 174 hours. Further within this definition, the number of rac-aminopterin doses in each cycle can range from 1 to 5, and each individual dose may comprise taking one or a plurality of individual dosage forms.

Thus, for example, one dose of rac-aminopterin is administered to a patient every 7 days for at least 4 cycles, and most preferably for at least 52 cycles (i.e., a year). In this case, the number of doses per cycle is only a single dose, the periodicity is 7 days, and the greatest duration between the last dose of one cycle and the first dose of the next cycle is 6 days. In another example, one dose of rac-aminopterin is administered on Monday and one on Tuesday for at least 52 cycles. In this case, the number of doses per cycle is 2, the periodicity is 7 days, and the greatest duration between the last dose of one cycle and the first dose of the next cycle is 5 days (i.e., Wednesday through Sunday). In yet another example, a dose of rac-aminopterin is administered in the morning and another at night on a particular day of the week by taking two tablets with each dose, this cycle is then repeated for at least 52 cycles. In this example, the number of doses per cycle is 2 wherein each dose comprises taking 2 dosage forms, the periodicity is 7 days, and the greatest duration between the last dose of one cycle and the first dose of the next cycle is 6 days (i.e., the days between the day of the week the doses is given). It will be understood that other schedules and examples are within the scope of this disclosure. For example, in one embodiment, one dose of rac-aminopterin is administered on Monday and one on Wednesday for at least 52 cycles. In this case, the number of doses per cycle is 2, the periodicity is 7 days, and the greatest duration between the last dose of one cycle and the first dose of the next cycle is 4 days (i.e., Thursday through Sunday). Most preferably, the periodicity is weekly (i.e., 7 days).

In still further examples, the weekly dose comprises a cumulative dose of rac-aminopterin ranging from 0.001-0.14 mg/kg, 0.010-0.06 mg/kg, and most preferably 0.020-0.06 mg/kg. For example, a 0.25 kg patient (e.g., a rat) would be administered between 0.00025 mg and 0.035 mg rac-aminopterin, between 0.0025 mg and 0.015 mg rac-aminopterin, and between 0.005 mg and 0.015 mg rac-aminopterin; whereas a 1.0 kg patient would be administered between 0.001 mg and 0.14 mg rac-aminopterin, between 0.010 mg and 0.06 mg rac-aminopterin, and between 0.02 mg and 0.06 mg rac-aminopterin; whereas a 100 kg patient would be administered between 0.1 mg and 14.0 mg rac-aminopterin, between 1.0 mg and 6.0 mg rac-aminopterin, and between 2.0 mg and 6.0 mg rac-aminopterin. For a typical 60 kg adult, the weekly dosage thus comprises a cumulative dose of rac-aminopterin ranging from 0.06-8.4 mg, 0.6-3.6 mg, and most preferably 1.2-3.6 mg.

The present disclosure further provides a method for treating a disorder in a patient using combination therapy, which comprises administering to said patient a therapeutically effective amount of rac-aminopterin or a pharmaceutically acceptable salt thereof, and administering involving at least one other therapeutic agent according to a protocol. The at least one other therapeutic agent may be administered prior to, contemporaneous with, or after administering the rac-aminopterin or a pharmaceutically acceptable salt thereof. The at least one other therapeutic agent also includes a single dosage form containing rac-aminopterin and at least one other therapeutic, a multiple dosage form, wherein the rac-aminopterin and the at least one other therapeutic are administered separately but concurrently, or a multiple dosage form wherein the two components are administered separately, but sequentially.

The at least one other therapeutic agent can be, for example, folic acid, L-aminopterin, leucovorin, dextromethorphan, memantine, prednisone, a cox-2 inhibitor, a non-steroidal anti-inflammatory drug, vincristine, dexamethasone, asparaginase, daunorubicin, mercaptopurine, etoposide, cytarabine, doxorubicin, cisplatin, ifosfamide, paclitaxel, 5-fluoruracil, diahydrogalacitol, tamoxifen, piperazinedione, mitoxantrone, diaziquone, aminothiadiazole, methotrexate, tenoposide, vincristine, echinomycin, 6-mercatopurine, dexamethasone, cyclophosphamide, soluble TNF receptors, anti-TNF antibodies, and anti-TNF humanized antibodies. In one embodiment, rac-aminopterin is administered together with L-aminopterin, or a pharmaceutically acceptable salt thereof, wherein the L-aminopterin is about 10% to about 90%, 20% to 80%, and more preferably 30% to 70%, by weight of the total aminopterin.

In a preferred embodiment, a dose of rac-aminopterin, from 0.001-0.3 mg/kg, 0.010-0.06 mg/kg, and most preferably 0.020-0.06 mg/kg, is suitable for use in a therapeutic protocol employed during a combination therapy. Preferably, rac-aminopterin is directly substituted for methotrexate in a therapeutic protocol employing methotrexate by administering rac-aminopterin at about 8-16% of the dose of methotrexate in the protocol.

In another preferred embodiment, rac-aminopterin is substituted for methotrexate in the treatment of adult rheumatoid arthritis in a therapeutic protocol employing another non-steroidal anti-inflammatory drug by administering a single weekly oral dose of 1 to 4 mg rac-aminopterin instead of a single weekly dose of 7-25 mg methotrexate.

In another embodiment, rac-aminopterin is substituted for methotrexate in the treatment of juvenile rheumatoid arthritis in a therapeutic protocol employing another non-steroidal anti-inflammatory drug by administering a single weekly oral dose of 0.5 to 2.2 mg/m$^2$ rac-aminopterin instead of a single weekly dose of 4-13 mg/m$^2$ methotrexate. In still another embodiment, psoriasis in an adult is treated in a therapeutic protocol by administering a single weekly oral dose of 1 to 4 mg rac-aminopterin instead of a single weekly dose of 15-25 mg methotrexate.

Rac-aminopterin and its disodium salt is prepared starting with folic acid, or most preferably racemic folic acid, as the feedstock using the process described in U.S. Pat. No. 7,235,660, the disclosure of which is incorporated by reference herein. Alternatively, rac-aminopterin and its disodium salt are prepared using the methods of Piper and Montgomery using racemic N-(p-aminobenzoyl)-glutamic acid (Piper and Montgomery, *J. Org. Chem.* 42:208, 1977; U.S. Pat. Nos. 4,077,957; 4,079,056; and 4,224,446, the disclosures of which are incorporated by reference herein). For example, beginning with readily available starting materials, rac-aminopterin may be synthesized according to Scheme 1.

Scheme 1

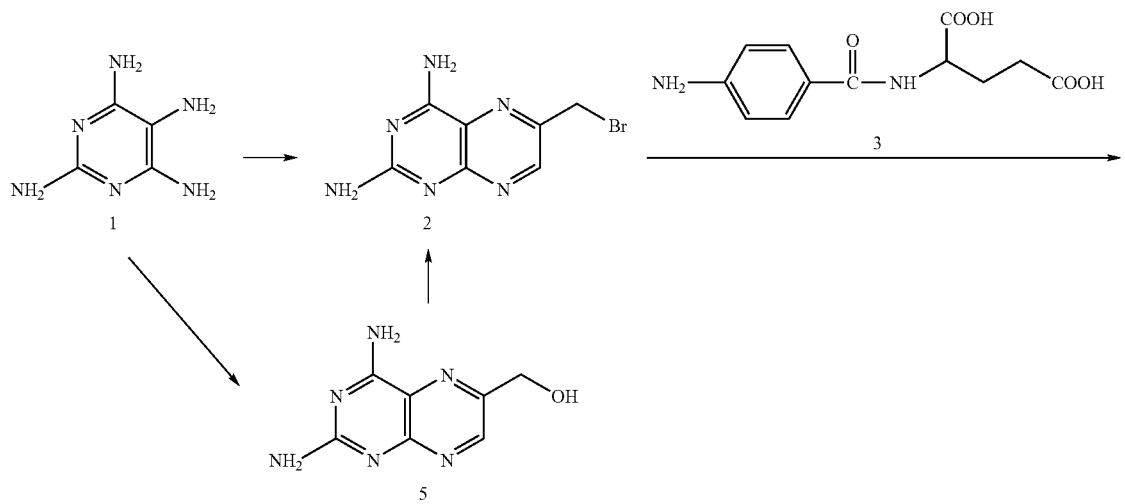

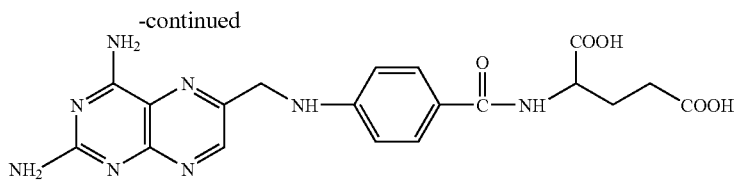

4

As illustrated above, the commercially available 2,4,5,6-tetraminopyrimidine, compound 1, may be condensed with β-bromopyruvaldoxime to provide 2,4-diamino-6-(bromomethyl)pteridine, compound 2 (Taghavi-Moghadam and Pfleiderer, *Tet. Lett.* 38:6835, 1997 and Taylor and Portnoy, *J. Org. Chem.* 38:806, 1973). Alternatively, compound 1 may be reacted with 1,3-dihydroxyacetone to provide 2,4-diamino-6-pteridinemethanol, compound 5 (Baugh and Shaw, *J. Org. Chem.* 29:3610, 1964). Compound 5 is purified and reacted with HBr and dibromotriphenylphosphorane ($Ph_3PBr_2$) in dimethylacetamide to afford compound 2 (Piper and Montgomery, *J. Org. Chem.* 42:208, 1977; Piper and Montgomery, *J. Heterocycl. Chem.* 11:279, 1974; Piper and Montgomery, U.S. Pat. No. 4,077,957; and Piper and Montgomery, U.S. Pat. No. 4,079,056). In still other embodiments, compound 2 can be arrived at via the reaction of compound 1 with 1,1-dichloroacetone to form 2,4-diamino-6-(methyl)pteridine, which is then reacted with bromide (Catalucci, U.S. Pat. No. 4,224,446).

Regardless of the route to its synthesis, compound 2 is condensed with N-(p-aminobenzoyl)-L/D-glutamic acid (i.e., racemic N-(p-aminobenzoyl)-glutamic acid), compound 3, in dimethylacetamide to afford rac-aminopterin, compound 4 (Piper and Montgomery, *J. Org. Chem.* 42:208, 1977; Piper and Montgomery, U.S. Pat. No. 4,077,957; Piper and Montgomery, U.S. Pat. No. 4,079,056; and Catalucci, U.S. Pat. No. 4,224,446). Compound 3 can be synthesized in the manner described by Hutchings et al, *J. Biol. Chem.* 1947, pg. 343. Briefly, p-nitrobenzoyl chloride is condensed with racemic glutamic acid in aqueous NaOH solution. The resulting p-nitrobenzoyl-rac-Glu is then reduced by catalytic hydrogenation ($H_2$, palladium on activated charcoal) to yield compound 3. There are many alternative methods to reduce an aromatic nitro group to an amine, which is known to one skilled in the art.

In addition to rac-aminopterin, the disclosed pharmaceutical compositions may contain one or more pharmaceutically acceptable carriers, and optionally other therapeutic ingredients. Pharmaceutical compositions are most readily prepared by combining rac-aminopterin in intimate admixture with one or more pharmaceutical carriers according to conventional pharmaceutical compounding techniques. Rac-aminopterin will typically comprise only a small percentage of the total pharmaceutical composition.

A pharmaceutical carrier may take a wide variety of forms depending on the form of the pharmaceutical composition (i.e., "preparation" or "form") desired for administration, e.g., oral or parenteral (including intravenous injections or infusions). In preparing the pharmaceutical composition in an oral dosage form any of the usual pharmaceutical carriers may be employed. Usual pharmaceutical carriers include, for example, water, glycols, oils, alcohols, flavoring agents, preservatives, coloring agents, and the like in the case of oral liquid preparations (such as for example, suspensions, solutions, and elixirs); aerosols; or carriers such as starches, sugars (e.g., lactose), microcrystalline cellulose, diluents, granulating agents, lubricants, binders, disintegrating agents and the like, in the case of oral solid preparations (such as for example, powders, capsules, and tablets) with the oral solid preparations generally being preferred over the oral liquid preparations. For pediatric patients, however, pleasant tasting oral liquid preparations are preferred.

Because of their ease of administration, tablets and capsules represent the most advantageous oral dosage form in adults, in which case solid pharmaceutical carriers are employed. If desired, tablets may be coated by standard aqueous or nonaqueous techniques. The parenteral dosage form can consist of a sterile solution of the active ingredient, either in its free or salt form, in physiological buffer or sterile water. In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

In addition to the common dosage forms set out above, the pharmaceutical compositions of the present disclosure may also be administered by controlled release means and/or delivery devices such as those described in U.S. Pat. Nos. 3,845,770; 3,916,899; 3,536,809; 3,598,123; 3,630,200; 4,008,719; 4,687,660 and 4,769,207, the disclosures of which are incorporated by reference herein.

Optionally, the pharmaceutical composition contains other therapeutic ingredients. Such therapeutic ingredients may be added to ameliorate certain side-effects, particularly those of rac-aminopterin, or add to patient convenience by reducing the number of dosage forms that must be taken. Suitable therapeutic ingredients for combining with the pharmaceutical composition may include, for example, folic acid, leucovorin, prednisone, a cox-2 inhibitor, a non-steroidal anti-inflammatory drug, vincristine, dexamethasone, asparaginase, daunorubicin, mercaptopurine, etoposide, cytarabine, doxorubicin, cisplatin, ifosfamide, paclitaxel, 5-fluoruracil, diahydrogalacitol, tamoxifen, piperazinedione, mitoxantrone, diaziquone, aminothiadiazole, methotrexate, tenoposide, vincristine, echinomycin, 6-mercatopurine, dexamethasone, cyclophosphamide, soluble TNF receptors, antibodies, and humanized antibodies.

As used in the methods and compositions of the present disclosure, the term "pharmaceutically acceptable salts" refers to salts prepared from pharmaceutically acceptable non-toxic acids or bases including inorganic acids and bases and organic acids and bases. The sodium or di-sodium salts of aminopterin are pharmaceutically acceptable salts of rac-aminopterin.

Since rac-aminopterin is both basic and acidic, salts are prepared from pharmaceutically acceptable non-toxic acids or bases including inorganic and organic acids or inorganic and organic bases. Such salts may contain any of the following anions: acetate, benzensulfonate, benzoate, camphorsulfonate, citrate, fumarate, gluconate, hydrobromide, hydrochloride, lactate, maleate, mandelate, mucate, nitrate, pamoate, phosphate, succinate, sulfate, tartrate and the like.

Such salts may also contain the following cations: aluminum, calcium, lithium, magnesium, potassium, sodium, zinc, benzathine, chloroprocaine, choline, diethanolamine, ethylenediamine, meglumine, and procaine.

Any suitable route of administration may be employed for providing a patient with a therapeutically effective amount of rac-aminopterin, or a pharmaceutically acceptable salt thereof. For example, oral, rectal, parenteral, transdermal, subcutaneous, intramuscular, and the like may be employed as appropriate. Dosage forms include tablets, coated tablets, troches, dispersions, suspensions, solutions, caplets, capsules, patches, and, the like. Pharmaceutical compositions include those suitable for oral, rectal and parenteral (including subcutaneous, intramuscular, and intravenous) administration, although the most suitable route in any given case will depend on the nature and severity of the disorder being treated. The most preferred route is the oral route. The pharmaceutical compositions may be conveniently presented in unit dosage form, and prepared by any of the methods well known in the art of pharmacy.

Pharmaceutical compositions of the present disclosure suitable for oral administration may be presented as discrete units such as capsules, cachets, or tablets, or aerosols sprays, each containing a predetermined amount of the pharmaceutically active ingredient, as a powder or granules, or as a solution or a suspension in an aqueous liquid, a non-aqueous liquid, an oil-in-water emulsion, or a water-in oil liquid emulsion. Such pharmaceutical compositions may be prepared by any of the methods of pharmacy, but all methods include the step of bringing into association the active pharmaceutical ingredient with at least one pharmaceutical carrier. In general, the pharmaceutical compositions are prepared by uniformly and intimately admixing the active pharmaceutical ingredient with liquid pharmaceutical carriers or finely divided solid pharmaceutical carriers or both, and then, if necessary, shaping the product into the desired presentation.

For example, a tablet may be prepared by compression or molding, optionally, with one or more accessory ingredients. Compressed tablets may be prepared by compressing in a suitable machine the active pharmaceutical ingredient in a free-flowing form such as powder or granules, optionally mixed with a binder, lubricant, inert diluent, surface active agent or dispersing agent. Molded tablets may be made by molding in a suitable machine, a mixture of the powdered compound moistened with an inert liquid diluent.

Desirably, each tablet contains from about 0.25 mg to about 4 mg of rac-aminopterin or a therapeutically acceptable salt thereof, and each cachet or capsule contains from about 0.25 mg to about 4 mg of rac-aminopterin or a therapeutically acceptable salt thereof. Most preferably, the tablet, cachet or capsule contains either one of two dosages, about 0.25 mg or about 1 mg of rac-aminopterin or a therapeutically acceptable salt thereof.

In other preferred embodiments, the dosage form contains 0.05 mg, 0.75 mg, 0.1 mg, 0.15 mg, 0.2 mg, 0.25 mg, 0.3 mg, 0.35 mg, 0.4 mg, 0.45 mg, 0.5 mg, 0.55 mg, 0.6 mg, 0.65 mg, 0.7 mg, 0.75 mg, 0.8 mg, 0.85 mg, 0.9 mg, 0.95 mg or 1.0 mg rac-aminopterin or therapeutically acceptable salt thereof. In still other embodiments the dosage form is a tablet. In another embodiment, the weekly dosage comprises taking one to three dosage forms by mouth of any dose combination thereof. The above cumulative weekly dose of rac-aminopterin can be given either in a single administration at a particular time, or as a plurality of administrations during a single day, or over multiple days. Using the methods of the present disclosure, it has been discovered that rac-aminopterin can be given to a patient with an inflammatory disorder without toxicity manifestations, and in the most preferred embodiments without interruption. In another preferred embodiment, the amount of rac-aminopterin, or pharmaceutically acceptable salt thereof, within a dosage form is between 0.00025 mg and 7.0 mg rac-aminopterin, more preferably between 0.00025 mg and 0.5 mg rac-aminopterin, more preferably between 0.00025 mg and 0.4 mg rac-aminopterin, more preferably between 0.00025 mg and 0.3 mg rac-aminopterin, more preferably between 0.00025 mg and 0.2 mg rac-aminopterin, and more preferably between 0.00025 mg and 0.1 mg rac-aminopterin. In preferred embodiments the dosage form is a tablet.

EXAMPLE 1

Pharmaceutical Compositions

Enantiomerically pure and racemic, scored, immediate release (IR) tablet formulations in dose strengths of 0.25 mg (batch 15710907) and 1.0 mg (batch 38711100 and batch 11610604) were prepared as in Table 1.

TABLE 1

|  | 1.0 mg tablet* | 1.0 mg tablet* | 0.25 mg tablet* |
|---|---|---|---|
| Batch | 38711100 | 11610604 | 15710907 |
| Aminopterin Isomer | L | L | L and D |
| Microcrystalline Cellulose | 52.11 mg | 52.11 mg | 50.92 mg |
| Lactose Monohydrate | 42.93 mg | 42.93 mg | 45.00 mg |
| Sodium Croscarmellose | 3.00 mg | 3.00 mg | 3.00 mg |
| Magnesium Stearate | 0.50 mg | 0.50 mg | 0.50 mg |
| Colloidal Silicon Dioxide | 0.25 mg | 0.25 mg | 0.25 mg |
| Tablet Weight | 100 mg | 100 mg | 100 mg |

*Claimed tablet dose strengths are stated in terms of free acid (i.e., diacid) equivalents of the L-isomer, or the L-isomer plus the D-isomer, although in all cases the drug substance in the tablet is the disodium salt.

EXAMPLE 2

Analysis of L and D Isomers in Tablet Formulations

An isocratic reverse-phase HPLC method with chiral mobile phase was employed to confirm the enantiomeric purity of the pure L-isomer tablet formulations (batch 38711100 and batch 11610604) and to determine the relative amounts of L and D isomers in the racemic tablet formulation (batch 15710907). The method comprised the following steps:

Step 1: Chiral Mobile Phase for Analytical HPLC. L-proline (1.86 g, 16 mmol, Sigma Aldrich product P-0380) and copper (II) nitrate hydrate (1.86 g, 8 mmol, Sigma Aldrich product 229636) were dissolved in 1.0 liter of filtered and degassed HPLC grade water (J. T. Baker product 4218-03). Using a pH meter, the pH of solution was brought to 6.00 using 5 N NaOH (approximately 2.5 ml).

Step 2: L-Aminopterin Standard Preparation. A 1.0 mg/ml solution of L-aminopterin (Sigma Aldrich product A1784) was prepared in dimethylacetamide. This was diluted 10-fold by adding 100 µl of this solution to 900 µl of the mobile phase (16 mM L-Pro and 8 mM Cu (II)), which provided a 0.1 mg/ml solution of L-aminopterin Standard Preparation for analysis.

Step 3: D-Aminopterin Standard Preparation. A 1.0 mg/ml solution of D-aminopterin (synthesized in house) was prepared in dimethylacetamide. This was diluted 10-fold by adding 100 µl of this solution to 900 µl of the mobile phase (16 mM L-Pro and 8 mM Cu (II)), which provided a 0.1 mg/ml solution of D-aminopterin Standard Preparation for analysis.

Step 4: System Suitability Preparation. A 50:50 mixture of L-aminopterin and D-aminopterin was prepared by mixing 500 µl of each 0.1 mg/ml standard from steps 2 and 3 above in the mobile phase, which provided a mixture L- and D-aminopterin, each at 0.05 mg/ml.

Step 5: Chromatographic System. The liquid chromatograph was equipped with a variable wavelength detector (VWD) set to monitor at 370 nm and a 2.0 mm×50 mm column (e.g., a Phenomenex Gemini, 110 Å, 5 µm, C18). Isocratic mobile phase conditions were 100% solvent A (16 mM L-Pro and 8 mM Cu (II), pH 6.0) at a flow rate is 0.6 ml/min. The column temperature was maintained at 60° C. during the analysis by use of a column oven.

Step 6: Procedure.

6a: Blank Baseline. A 5 µl sample of diluent (10% aq. dimethylacetamide) was injected into the chromatograph, and the chromatogram and the peak responses was recorded. The peaks obtained were defined as the ones present in the blank injection, and their area recorded. They were excluded from any subsequent area calculations.

6b: Standard and Suitability Preparations. A 5 µl aliquot of the D-aminopterin Standard Preparation, D-aminopterin Standard Preparation and the System Suitability Solution were separately injected into the chromatograph, and the chromatograms and the peak responses recorded. The area of the peaks in the chromatogram not present in the blank, were recorded. System suitability was met when: (1) the L- and D-aminopterin resolved from one another with a resolution R between peaks of not less than 1.5, (2) there was no discernable L- and D-peak in the pure D- and L-standard, respectively, and (3) for the 50:50 mixture, a peak area RSD of 6 replicate injections was not more than 1.0%, and the ratio of the mean L- to D-peak area for 6 replicate injections was 0.98-1.02.

6c: Sample. A tablet formulation was immersed in water to provide a 1 mg/ml solution that was then diluted 10-fold with water to provide a test sample. A 5 µl aliquot of the test sample was injected in 3 replicates. The mean peak area for the L- and D-peaks was calculated. The percentage of each was calculated from the mean values. If there was no discernable L- or D-peak, 0% was reported.

TABLE 2

|  | 1.0 mg tablet | 1.0 mg tablet | 0.25 mg tablet |
| --- | --- | --- | --- |
| Batch | 387I1100 | 116I0604 | 157I0907 |
| Aminopterin Isomer | L | L | L and D |
| L-isomer | 100% | 100% | 68% |
| D-isomer | 0% | 0% | 32% |

Using this procedure, the enantiomeric purity of the pure L-isomer tablet formulations (batch 387I1100 and batch 116I0604) was confirmed, and the relative amounts of L and D isomers in the racemic tablet formulation (batch 157I0907) was determined as summarized in Table 2.

EXAMPLE 3

Quantitation of Total Aminopterin Isomers in Tablet Formulations

A reverse-phase HPLC gradient method was employed to assay the total quantity of aminopterin isomers in the pure L-isomer tablet formulations (batch 387I1100 and batch 116I0604) and in the racemic tablet formulation (batch 157I0907). The method comprised the following steps:

Step 1: Mobile Phase Preparation. A 1 L solution of filtered and degassed 0.1 M triethylammonium acetate buffer was prepared by dissolving 100 ml of 1.0 M triethylammonium acetate buffer (1.0 M TEAAC, Fluka product 90357) in 900 ml of HPLC grade water as solvent A and 1 L of filtered and degassed acetonitrile was prepared as solvent B.

Step 2: L-Aminopterin Standard. An amount of (50 mg×565.2/440.4) of L-aminopterin standard (the disodium salt) was weighed (i.e., an amount equivalent to 50 mg of the free acid). The L-aminopterin standard was then transferred to a 50 ml volumetric flask and dissolved in solvent A to a volume of 50 ml to provide a 1.0 mg/ml solution (free acid equivalent). This was then diluted 10-fold by adding 100 W of this solution to 900 W of solvent A to provide a 0.1 mg/ml solution.

Step 3: Chromatographic system. The liquid chromatograph was equipped with a Variable Wavelength Detector (VWD) set at 260 nm, and a 2.0 mm×50 mm column (e.g., Phenomenex Gemini 110 Å, 5 µm, C18). Mobile phase conditions were 95% solvent A (0.1 M TEAAC): 5% solvent B (Acetonitrile) to 5% solvent A (0.1 M TEAAC): 95% solvent B over 30 minutes, hold at 95% solvent B for 10 minutes, and re-equilibrate at 95% solvent A: 5% solvent B for 15 minutes. The flow rate was 0.200 ml/min.

Step 4: Procedure.

4a: Baseline Response. An aliquot of 5 µl of solvent A was injected into the chromatograph, and the chromatograms and the peak responses were recorded. The peaks obtained were defined as the ones present in the blank injection, and their area recorded. They were excluded from any subsequent area calculations.

4b: Standard Response. A 5 µl aliquot of the L-aminopterin standard was injected into the chromatograph in triplicate, and the chromatogram and the mean peak area responses recorded. The standard elutes at approximately 7 minutes, and L and D isomers co-elute in this non-chiral method.

4c: Sample Response. Tablet formulations were dissolved in solvent A as follows: batch 157I0907, 10 tablets per 5 ml water (0.5 mg/ml); and batch 387I1100 and batch 116I0604, 5 tablets per 20 ml water (0.25 mg/ml). After centrifugation, a 5 µl aliquot of the supernatant from each formulation was injected in triplicate. The mean and standard deviation (SD) of the peak area for aminopterin was then calculated for each tablet, and divided by the mean peak area of the standard to obtain the amount of aminopterin in each tablet.

Using this procedure, the total aminopterin in the pure L-isomer tablet formulations (batch 387I1100 and batch 116I0604) and the racemic tablet formulation (batch 157I0907) was quantitated as summarized in Table 3.

TABLE 3

|  | 1.0 mg scored tablet | 1.0 mg scored tablet | 0.25 mg scored tablet |
|---|---|---|---|
| Batch | 387I1100 | 116I0604 | 157I0907 |
| Aminopterin Isomer | L | L | L and D |
| Tablet Equivalents | 1 | 1 | 4 |
| L-isomer measured (±SD) | 0.8875 ± 0.0029 mg | 0.8462 ± 0.0018 mg | 0.7018 ± 0.0044 mg |
| D-isomer measured (±SD) | — | — | 0.3282 ± 0.0021 mg |
| Percent of Label Claim | 89% | 85% | 103% |

EXAMPLE 4

Pharmacokinetics and Absorption in Beagle Dogs

Ten (N=10) Beagle dogs were enrolled in a pharmacokinetic study to examine the oral absorption of 1 tablet of the pure L-isomer tablet formulation (batch 116I0604), 1 mg of the D-isomer admixed with 99 mg microcrystalline cellulose, and 4 tablets of the racemic tablet formulation (batch 157I0907). Each formulation was encapsulated in a hard gelatin capsule and administered by direct gastric placement. Dosing of each formulation was separated by a 7 day washout period. The mean body weight of the ten dogs was 11.3±1.7 (SD) kilograms.

For pharmacokinetic analysis, venous blood samples with EDTA as anticoagulant were taken before each dosing and at 0.5, 1, 1.5, 2, 3, 6, 9 and 12 hours after each dosing. Samples were centrifuged, and the plasma collected and frozen for analysis. There was no urine sampling in this study. Aminopterin in plasma samples was quantitated by an achiral LC/MS assay (Advion Biosciences, Ithaca, N.Y.). The lower limit of quantitation (LLOQ) of the assay was 0.5 ng/ml or 1.2 nM. The amount of L-isomer and D-isomer in plasma samples from animals dosed with the racemate was determined using a chiral LC/MS assay.

Figure 2:
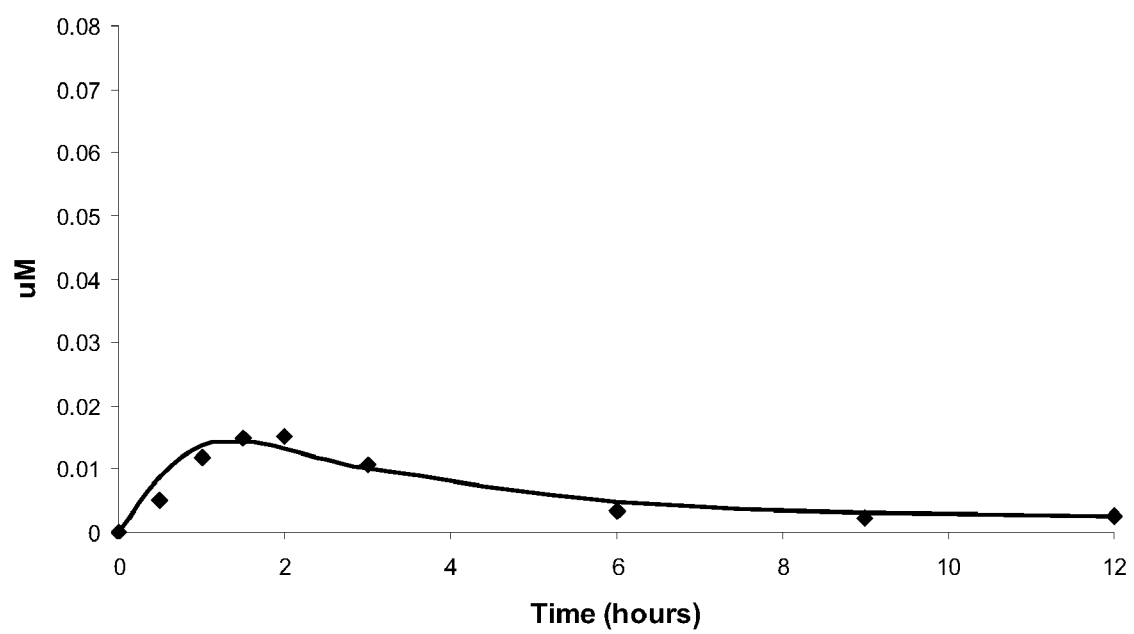
FIG. 2 is a graphical depiction of the mean plasma levels of the D-isomer following oral administration of D-aminopterin to 10 Beagle dogs described in Example 4.
Figure 3:
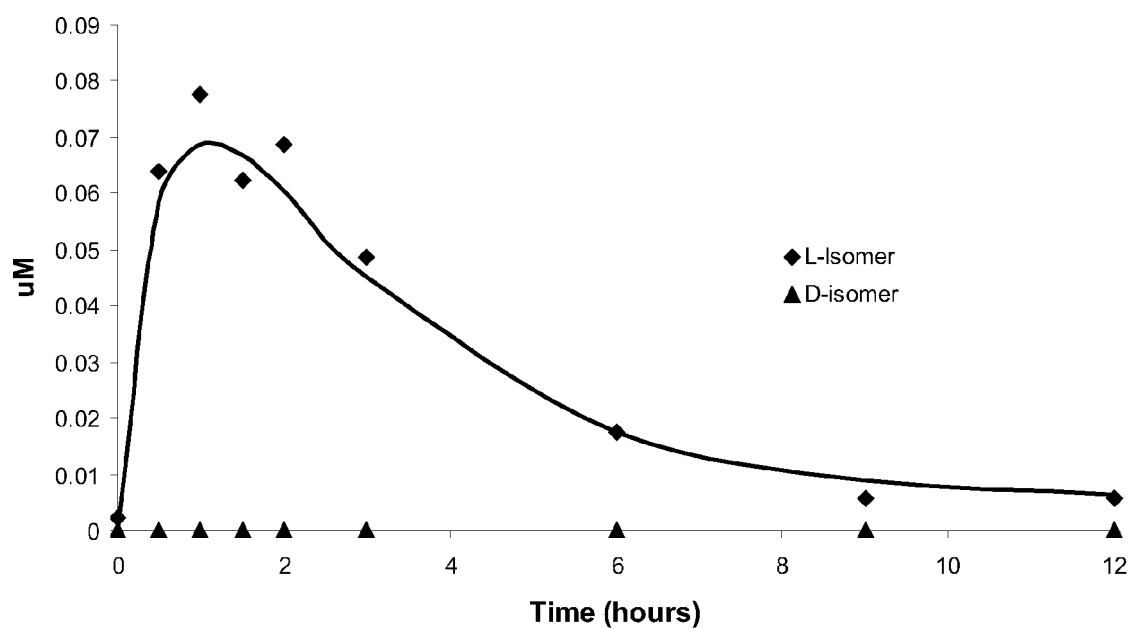
FIG. 3 is a graphical depiction of the mean plasma levels of the L-isomer and D-isomer following oral administration of racemic aminopterin to 10 Beagle dogs described in Example 4.

The mean plasma concentrations (N=10 for each formulation) of each isomer for each formulation administered are summarized in Table 4 and shown graphically in FIG. 1, FIG. 2 and FIG. 3. These data show that when given separately, both the L-isomer and the D-isomer were efficiently absorbed, although the systemic exposure of the D-isomer was approximately 30% that of the L-isomer (i.e., the AUC ratio). Unexpectedly however, when the L and D isomers were given together as the racemate combination, there was no systemic exposure of the D-isomer consistent with absorption being stereoselective for the L-isomer.

TABLE 4

| | L-isomer (Batch 116I0604) 0.85 mg L-isomer | D-isomer 1 mg D-isomer | Racemic (Batch 157I0907) 0.70 mg L-isomer 0.33 mg D-isomer | |
|---|---|---|---|---|
| Collection Time (hr) | Mean Plasma L-isomer (µM) | Mean Plasma D-isomer (µM) | Mean Plasma L-isomer (µM) | Mean Plasma D-isomer (µM) |
| 0.0 | 0.0000 | 0.0000 | 0.0000 | 0.0000 |
| 0.5 | 0.0328 | 0.0050 | 0.0639 | 0.0000 |
| 1.0 | 0.0629 | 0.0117 | 0.0776 | 0.0000 |
| 1.5 | 0.0680 | 0.0150 | 0.0624 | 0.0000 |
| 2.0 | 0.0535 | 0.0152 | 0.0686 | 0.0000 |
| 3.0 | 0.0353 | 0.0106 | 0.0487 | 0.0000 |
| 6.0 | 0.0125 | 0.0034 | 0.0175 | 0.0000 |
| 9.0 | 0.0048 | 0.0023 | 0.0058 | 0.0000 |
| 12.0 | 0.0041 | 0.0026 | 0.0056 | 0.0000 |

Figure 4:
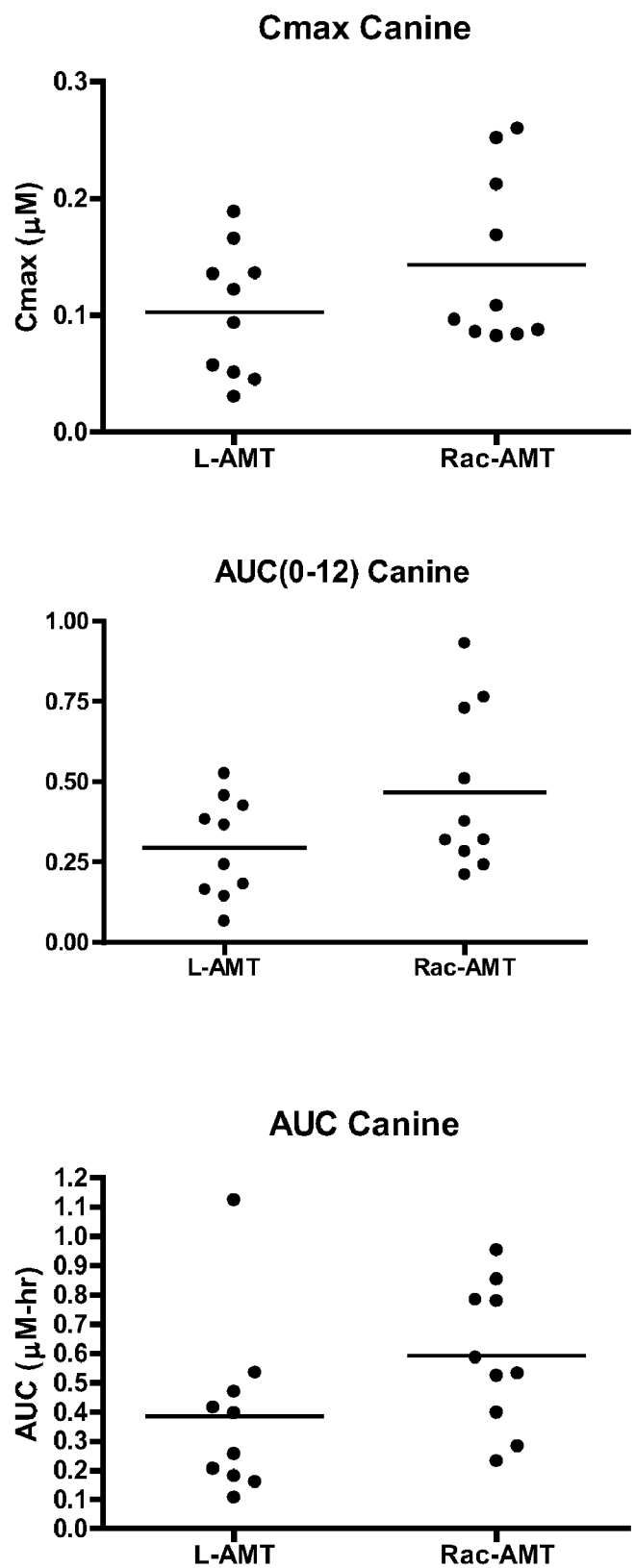
FIG. 4 is a graphical depiction of the $C_{max}$, $AUC_{(0-12\ hrs)}$ and $AUC_\infty$ values following oral administration of L-aminopterin and racemic aminopterin to each of the 10 Beagle dogs described in Example 4.

The pharmacokinetic parameters (dose-normalized to the amount of L-isomer administered) from this study for the formulations containing the L-isomer are summarized in Table 5. The values for the $C_{max}$, $AUC_{(0-12\ hrs)}$ and $AUC_\infty$ are plotted in FIG. 4. Also unexpectedly, the data show that the systemic exposure of the L-isomer was significantly enhanced (as measured by the $C_{max}$, $AUC_{(0-12\ hrs)}$ and $AUC_\infty$) from the racemic formulation compared to its absorption from the formulation containing only the L-isomer (P<0.05 for all three pharmacokinetic parameters, paired t-test).

TABLE 5

| | Batch 116I0604 (L-isomer) | | | Batch 157I0907 (racemic) | | |
|---|---|---|---|---|---|---|
| Subject | $C_{max}$ (µM) | $AUC_{(0-12\ hrs)}$ (µM-hr) | $AUC_\infty$ (µM-hr) | $C_{max}$ (µM) | $AUC_{(0-12\ hrs)}$ (µM-hr) | $AUC_\infty$ (µM-hr) |
| 945 | 0.165 | 0.457 | 0.468 | 0.168 | 0.510 | 0.523 |
| 946 | 0.136 | 0.425 | 1.125 | 0.212 | 0.729 | 0.784 |
| 947 | 0.188 | 0.526 | 0.533 | 0.251 | 0.764 | 0.779 |
| 948 | 0.122 | 0.366 | 0.415 | 0.260 | 0.931 | 0.953 |
| 949 | 0.045 | 0.145 | 0.160 | 0.108 | 0.377 | 0.397 |
| 950 | 0.030 | 0.066 | 0.106 | 0.087 | 0.242 | 0.281 |
| 951 | 0.051 | 0.165 | 0.180 | 0.096 | 0.283 | 0.530 |
| 952 | 0.135 | 0.384 | 0.395 | 0.082 | 0.320 | 0.853 |
| 953 | 0.057 | 0.182 | 0.204 | 0.086 | 0.319 | 0.585 |
| 954 | 0.093 | 0.243 | 0.255 | 0.083 | 0.211 | 0.231 |
| mean | 0.102 | 0.296 | 0.384 | 0.143 | 0.469 | 0.592 |

EXAMPLE 5

Pharmacokinetics and Absorption in Humans

Male and female subjects with moderate to severe psoriasis, 21 years of age or older were enrolled in randomized, single-dose, two-period cross-over study to compare the oral pharmacokinetics and safety of the 0.25 mg rac-aminopterin tablet (D and L aminopterin, batch 157I0907) with the 1.0 mg reference L-aminopterin tablet (batch 387I1100). Subjects were randomized to two parallel arms (N=6 each) to ingest a 1.0 mg single dose of either the rac-aminopterin tablets (4×0.25 mg tablets) or the reference L-aminopterin tablet (1×1.0 mg tablet), and blood specimens were obtained from each subject for 10 hours. Seven days later subjects of both arms were then crossed-over to the other arm of the trial and received a single oral 1.0 mg dose of the other formulation and again blood specimens were obtained over 10 hours.

The endpoint analysis included the $AUC_{(0-12\ hrs)}$, $AUC_\infty$ and $C_{max}$ of aminopterin in the plasma. The plasma was further subjected to chiral analysis to determine the extent to which the L and D isomers were differentially absorbed. Aminopterin in plasma samples was quantitated by an achiral LC/MS assay (Advion Biosciences, Ithaca, N.Y.). The lower limit of quantitation (LLOQ) of the assay was 0.5 ng/ml or 1.2 nM. The amount of L-isomer and D-isomer in plasma samples from animals dosed with the racemate was determined using a chiral LC/MS assay.

As was the case in the canine species, only the L-isomer was detected in the plasma from both formulations, consistent with intestinal absorption of the racemate being stereoselective for the L-isomer. The pharmacokinetic parameters (dose-normalized to the amount of L-isomer administered) from this study for the two formulations are summarized in Table 6.

TABLE 6

| | Batch 387I1100 (L-isomer) | | | Batch 157I0907 (racemic) | | |
|---|---|---|---|---|---|---|
| Subject | $C_{max}$ (µM) | $AUC_{(0-12\ hrs)}$ (µM-hr) | $AUC_\infty$ (µM-hr) | $C_{max}$ (µM) | $AUC_{(0-12\ hrs)}$ (µM-hr) | $AUC_\infty$ (µM-hr) |
| 101 | 0.053 | 0.155 | 0.164 | 0.129 | 0.305 | 0.323 |
| 102 | 0.149 | 0.405 | 0.445 | 0.142 | 0.380 | 0.394 |
| 103 | 0.045 | 0.217 | 0.256 | 0.049 | 0.194 | 0.224 |
| 104 | 0.095 | 0.219 | 0.228 | 0.155 | 0.321 | 0.339 |
| 105 | 0.086 | 0.282 | 0.302 | 0.120 | 0.372 | 0.405 |
| 106 | 0.058 | 0.197 | 0.212 | 0.089 | 0.267 | 0.278 |
| mean | 0.081 | 0.246 | 0.268 | 0.114 | 0.306 | 0.327 |

Figure 5:
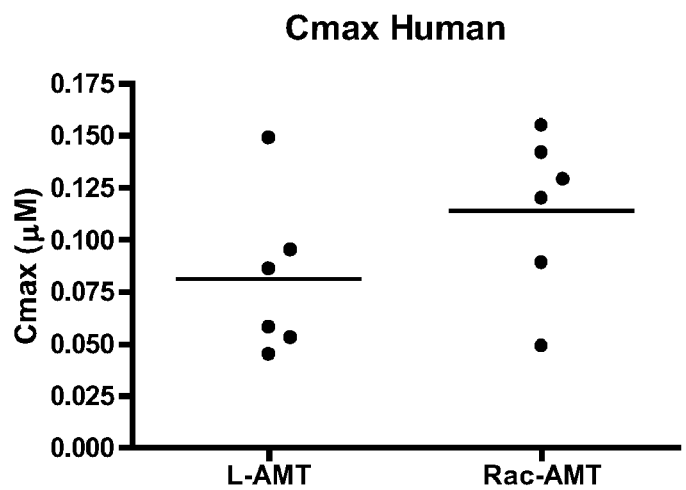
FIG. 5 is a graphical depiction of the $C_{max}$, $AUC_{(0-12\ hrs)}$ and $AUC_\infty$ values following oral administration of L-aminopterin and racemic aminopterin to each of the 6 human subjects described in Example 5.
Figure 5:
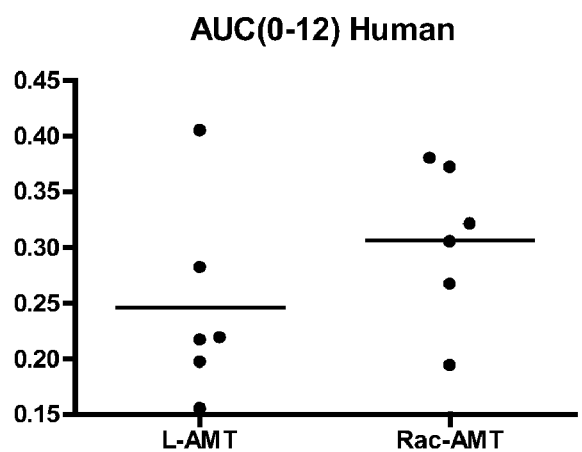
Figure 5:
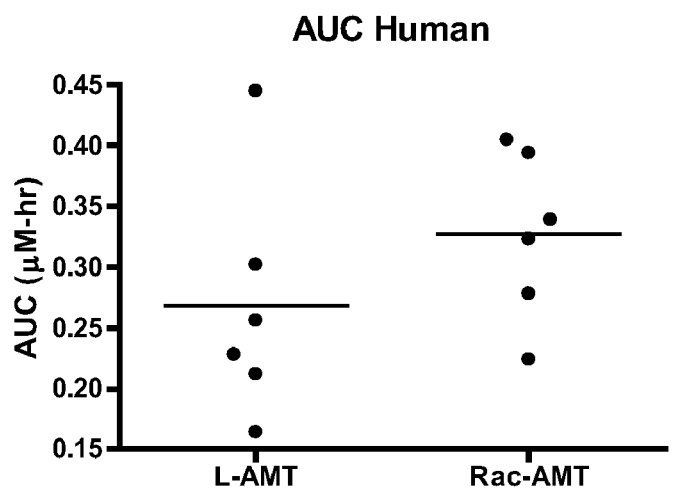

The values for the $C_{max}$, $AUC_{(0-12\ hrs)}$ and $AUC_\infty$ are plotted in FIG. 5. Also unexpectedly in humans as in dogs, the data show that the systemic exposure of the L-isomer was enhanced (as measured by the $C_{max}$, $AUC_{(0-12\ hrs)}$ and $AUC_\infty$ from the racemic formulation compared to its absorption from the formulation containing only the L-isomer.

While the disclosure has been described with particular reference to certain embodiments thereof, it will be understood that changes and modifications may be made by those of ordinary skill within the scope and spirit of the following claims:

The invention claimed is:

1. A pharmaceutical composition comprising from 10% to 90% (by weight) of L-aminopterin or a pharmaceutically acceptable salt thereof and from 10% to 90% (by weight) of D-aminopterin or a pharmaceutically acceptable salt thereof.

2. The pharmaceutical composition of claim 1 wherein the pharmaceutical composition is adapted for oral administration.

3. The pharmaceutical composition of claim 1 wherein the pharmaceutically acceptable salt of L-aminopterin or D-aminopterin is a disodium salt.

4. The pharmaceutical composition of claim 1, wherein the amount of total aminopterin is from 0.01 mg to 4 mg.

5. The pharmaceutical composition of claim 1, in the form of a tablet or capsule.

6. The pharmaceutical composition of claim 1, wherein the pharmaceutical composition comprises from 15% to 85% (by weight) of L-aminopterin or a pharmaceutically acceptable salt thereof and from 15% to 85% (by weight) of D-aminopterin or a pharmaceutically acceptable salt thereof.

7. The pharmaceutical composition of claim 6, wherein the pharmaceutical composition comprises from 25% to 75% (by weight) of L-aminopterin or a pharmaceutically acceptable salt thereof and from 25% to 75% (by weight) of D-aminopterin or a pharmaceutically acceptable salt thereof.

8. The pharmaceutical composition of claim 7, wherein the pharmaceutical composition comprises from 35% to 65% (by weight) of L-aminopterin or a pharmaceutically acceptable salt thereof and from 35% to 65% (by weight) of D-aminopterin or a pharmaceutically acceptable salt thereof.

9. The pharmaceutical composition of claim 8, wherein the pharmaceutical composition comprises from 45% to 55% (by weight) of L-aminopterin or a pharmaceutically acceptable salt thereof and from 45% to 55% (by weight) of D-aminopterin or a pharmaceutically acceptable salt thereof.

10. A method for treating a disorder in a patient comprising administering to the patient a therapeutically effective amount of a pharmaceutical composition comprising from 10% to 90% (by weight) of L-aminopterin or a pharmaceutically acceptable salt thereof and from 10% to 90% (by weight) of D-aminopterin or a pharmaceutically acceptable salt thereof.

11. The method of claim 10 wherein the therapeutically effective amount of total aminopterin is administered orally.

12. The method of claim 10 wherein the disorder is selected from the group consisting of rheumatoid arthritis, juvenile rheumatoid arthritis, psoriasis, psoriatic arthritis, arthritis, atopic dermatitis, inflammatory bowel disease, bronchopulmonary dysplasia, and canine atopic dermatitis.

13. The method of claim 10 further comprising using a second drug in a combination therapy.

14. The method of claim 13 wherein the second drug is folic acid.

15. The method of claim 10 wherein the therapeutically effective amount of aminopterin in the pharmaceutical composition is less than 0.3 mg total aminopterin per kilogram of patient body weight.

16. A method for treating disorders modulated by at least dihydrofolate reductase activity, said method comprising administering to a patient in need thereof a therapeutically effective amount of a pharmaceutical composition comprising from 10% to 90% (by weight) of L-aminopterin or a pharmaceutically acceptable salt thereof and from 10% to 90% (by weight) of D-aminopterin, or a pharmaceutically acceptable salt thereof.

17. The method of claim 16, wherein the therapeutically effective amount of the pharmaceutical composition is administered orally.

18. The method of claim 16, wherein the disorder is selected from the group consisting of leukemia, lymphoma, breast cancer, rheumatoid arthritis, juvenile rheumatoid arthritis, psoriasis, psoriatic arthritis, arthritis, atopic dermatitis, inflammatory bowel disease, bronchopulmonary dysplasia, and canine atopic dermatitis.

* * * * *